(12) United States Patent
Marczyk et al.

(10) Patent No.: US 8,540,132 B2
(45) Date of Patent: Sep. 24, 2013

(54) TILT ANVIL ASSEMBLY

(75) Inventors: Stanislaw Marczyk, Stratford, CT (US); Keith L. Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 2031 days.

(21) Appl. No.: 11/434,713

(22) Filed: May 16, 2006

(65) Prior Publication Data

US 2008/0230581 A1 Sep. 25, 2008

(51) Int. Cl.
*A61B 17/04* (2006.01)

(52) U.S. Cl.
USPC .................. 227/179.1; 227/176.1; 227/175.1; 606/219

(58) Field of Classification Search
USPC ...................... 227/175.1–182.1, 19
See application file for complete search history.

(56) References Cited

U.S. PATENT DOCUMENTS

| | | |
|---|---|---|
| 3,388,847 A | 6/1968 | Kasulin et al. |
| 3,552,626 A | 1/1971 | Astafiev |
| 3,638,652 A | 2/1972 | Kelley |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,754,909 A | 7/1988 | Barker et al. |
| 4,817,847 A | 4/1989 | Redtenbacher et al. |
| 4,873,977 A | 10/1989 | Avant et al. |
| 4,893,662 A | 1/1990 | Gervasi |

(Continued)

FOREIGN PATENT DOCUMENTS

| | | |
|---|---|---|
| CA | 908529 | 8/1972 |
| EP | 0152382 | 8/1985 |

(Continued)

*Primary Examiner* — Lindsay Low

(57) ABSTRACT

A tilt anvil assembly is disclosed which includes a center rod and a head assembly pivotally mounted to the center rod. The head assembly includes a housing, a post, an anvil plate and a backup member. The backup member is movable about the post from a first position preventing pivotal movement of the head assembly to a second position accommodating pivotal movement of the head assembly. A pivotal latch assembly is also provided to prevent movement of the backup member from its second position to its first position.

17 Claims, 7 Drawing Sheets

(56) References Cited

U.S. PATENT DOCUMENTS

| | | |
|---|---|---|
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,623,227 B2 | 9/2003 | Scott et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,716,222 B2 | 4/2004 | McAlister et al. |
| 6,716,233 B1 | 4/2004 | Whitman |
| 6,742,692 B2 | 6/2004 | Hartwick |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,827,246 B2 | 12/2004 | Sullivan et al. |
| 6,840,423 B2 | 1/2005 | Adams et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,981,941 B2 | 1/2006 | Whitman et al. |
| 7,032,798 B2 | 4/2006 | Whitman et al. |
| 7,059,331 B2 | 6/2006 | Adams et al. |

| | | |
|---|---|---|
| 7,059,510 B2 | 6/2006 | Orban, III |
| 7,080,769 B2 | 7/2006 | Vresh et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,168,604 B2 | 1/2007 | Milliman et al. |
| 7,179,267 B2 | 2/2007 | Nolan et al. |
| 7,182,239 B1 | 2/2007 | Myers |
| 7,303,106 B2 * | 12/2007 | Milliman et al. .......... 227/175.1 |
| 7,364,060 B2 * | 4/2008 | Milliman ................... 227/175.1 |
| 2001/0000903 A1 | 5/2001 | Heck et al. |
| 2001/0010320 A1 | 8/2001 | Bolduc et al. |
| 2001/0054636 A1 | 12/2001 | Nicolo |
| 2002/0020732 A1 | 2/2002 | Adams et al. |
| 2002/0047036 A1 | 4/2002 | Sullivan et al. |
| 2002/0063143 A1 | 5/2002 | Adams et al. |
| 2002/0185516 A1 | 12/2002 | Heck et al. |
| 2002/0185517 A1 | 12/2002 | Vresh et al. |
| 2003/0019905 A1 | 1/2003 | Adams et al. |
| 2003/0047582 A1 | 3/2003 | Sonnenschein et al. |
| 2003/0057251 A1 | 3/2003 | Hartwick |
| 2003/0065342 A1 | 4/2003 | Nobis et al. |
| 2003/0073981 A1 | 4/2003 | Whitman et al. |
| 2003/0089757 A1 | 5/2003 | Whitman |
| 2003/0111507 A1 | 6/2003 | Nunez |
| 2003/0127491 A1 | 7/2003 | Adams et al. |
| 2003/0132267 A1 | 7/2003 | Adams et al. |
| 2003/0144675 A1 | 7/2003 | Nicolo |
| 2003/0178465 A1 | 9/2003 | Bilotti et al. |
| 2003/0183671 A1 | 10/2003 | Mooradian et al. |
| 2003/0192936 A1 | 10/2003 | Hartwick |
| 2003/0192937 A1 | 10/2003 | Sullivan et al. |
| 2003/0201301 A1 | 10/2003 | Bolduc et al. |
| 2003/0218047 A1 | 11/2003 | Sharma et al. |
| 2003/0222117 A1 | 12/2003 | Orban, III |
| 2004/0092960 A1 | 5/2004 | Abrams et al. |
| 2004/0092974 A1 | 5/2004 | Gannoe et al. |
| 2004/0118896 A1 | 6/2004 | Sharma et al. |
| 2004/0134964 A1 | 7/2004 | Adams et al. |
| 2004/0153124 A1 | 8/2004 | Whitman |
| 2004/0232198 A1 | 11/2004 | Adams et al. |
| 2005/0051597 A1 | 3/2005 | Tolendano |
| 2005/0067454 A1 | 3/2005 | Vresh et al. |
| 2005/0087580 A1 | 4/2005 | Orban, III |
| 2005/0107813 A1 | 5/2005 | Gilete Garcia |
| 2005/0116009 A1 | 6/2005 | Milliman |
| 2005/0125009 A1 | 6/2005 | Perry et al. |
| 2005/0143758 A1 | 6/2005 | Abbott et al. |
| 2005/0145674 A1 | 7/2005 | Sonnenschein et al. |
| 2005/0145675 A1 | 7/2005 | Hartwick et al. |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0047308 A1 | 3/2006 | Ortiz et al. |
| 2006/0085032 A1 | 4/2006 | Viola |
| 2006/0085033 A1 | 4/2006 | Criscuolo et al. |
| 2006/0085034 A1 | 4/2006 | Bettuchi |
| 2006/0085035 A1 | 4/2006 | Viola |
| 2006/0097025 A1 | 5/2006 | Milliman et al. |
| 2006/0108393 A1 | 5/2006 | Heinrich et al. |
| 2006/0144897 A1 | 7/2006 | Jankowski et al. |
| 2006/0151567 A1 | 7/2006 | Roy |
| 2006/0191975 A1 | 8/2006 | Adams et al. |
| 2006/0201989 A1 | 9/2006 | Ojeda |
| 2006/0201993 A1 | 9/2006 | Hur |
| 2006/0241692 A1 | 10/2006 | McGuckin, Jr. et al. |
| 2006/0255090 A1 | 11/2006 | Milliman et al. |
| 2006/0289601 A1 | 12/2006 | Orban, III |
| 2007/0023475 A1 | 2/2007 | Csiky |
| 2007/0027473 A1 | 2/2007 | Vresh et al. |
| 2007/0029363 A1 | 2/2007 | Popov |
| 2007/0034666 A1 | 2/2007 | Holsten et al. |
| 2007/0034667 A1 | 2/2007 | Holsten et al. |
| 2007/0034668 A1 | 2/2007 | Holsten et al. |
| 2007/0038248 A1 | 2/2007 | Heinrch |
| 2007/0060952 A1 | 3/2007 | Roby et al. |

FOREIGN PATENT DOCUMENTS

| | | |
|---|---|---|
| EP | 0173451 | 3/1986 |
| EP | 0190022 | 8/1986 |
| EP | 282157 | 9/1988 |
| EP | 0503689 | 9/1992 |
| GB | 1185292 | 3/1970 |
| GB | 2016991 | 9/1979 |
| GB | 2070499 | 9/1981 |
| WO | 8706448 | 11/1987 |
| WO | 8900406 | 1/1989 |
| WO | 9006085 | 6/1990 |
| WO | WO 2004032766 A2 * | 4/2004 |

* cited by examiner

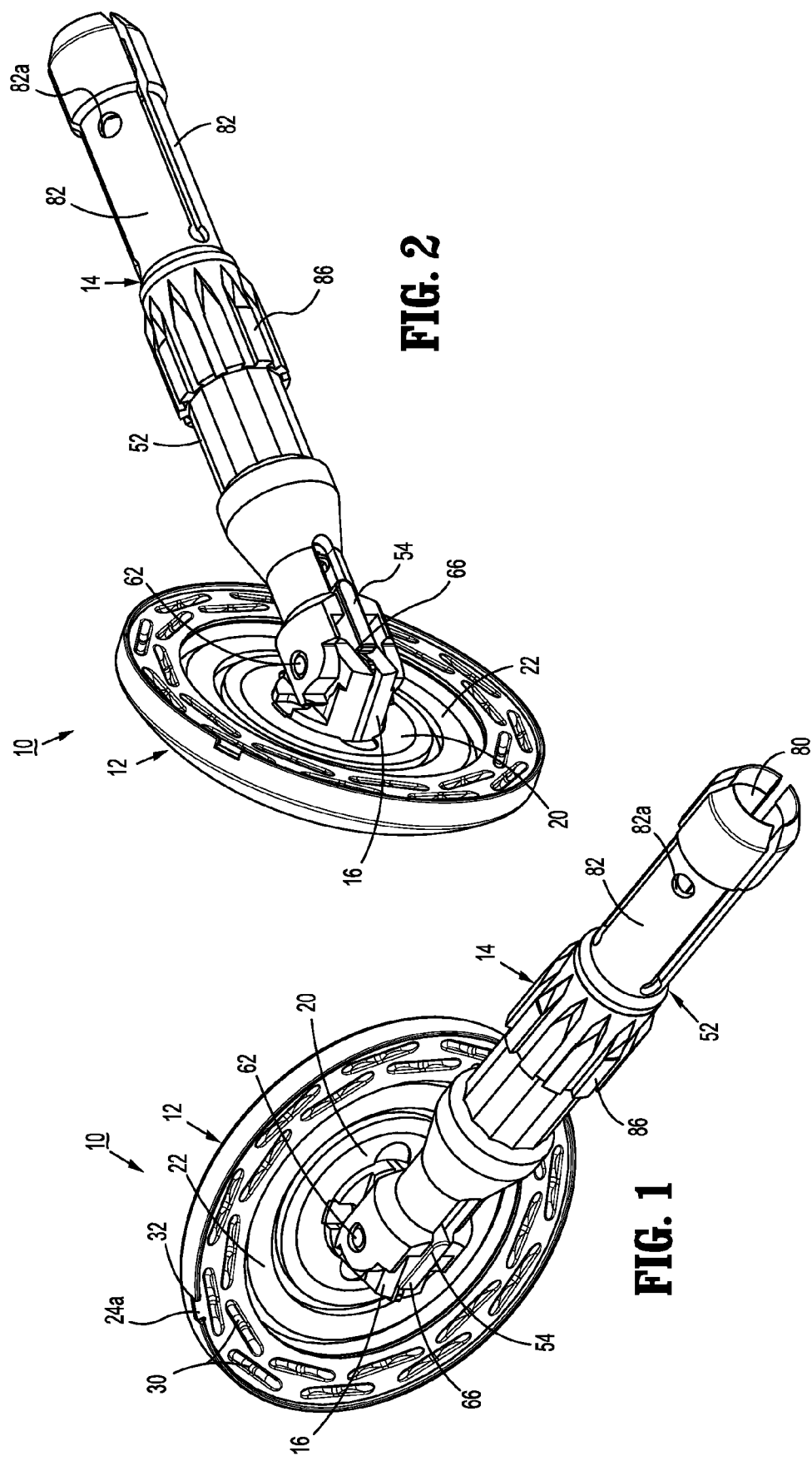

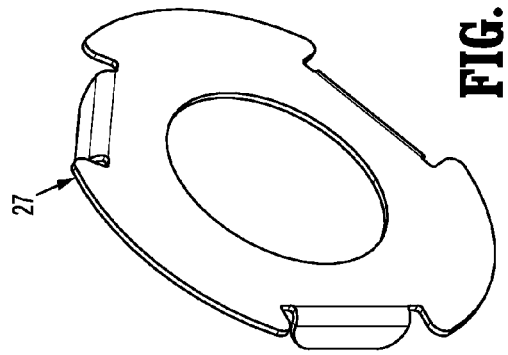
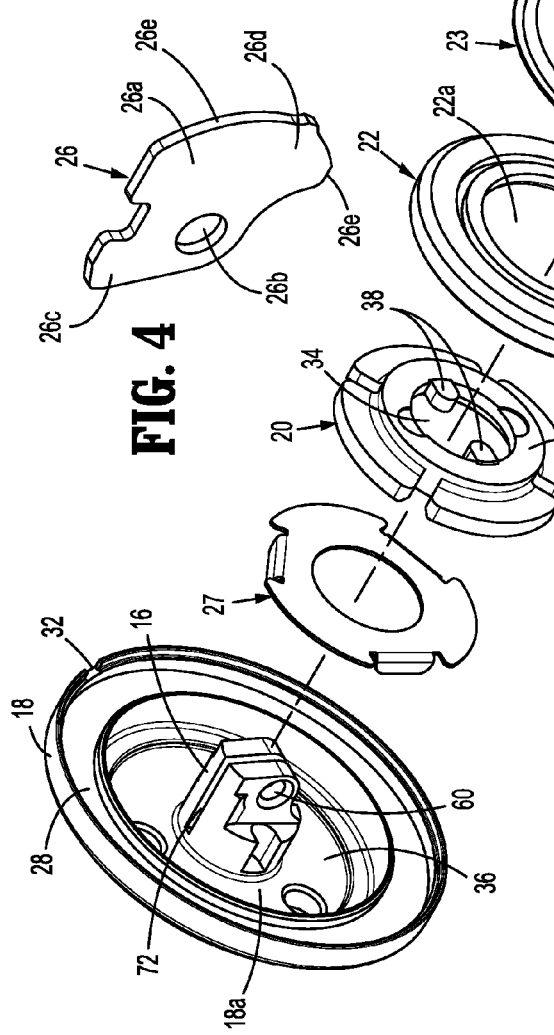
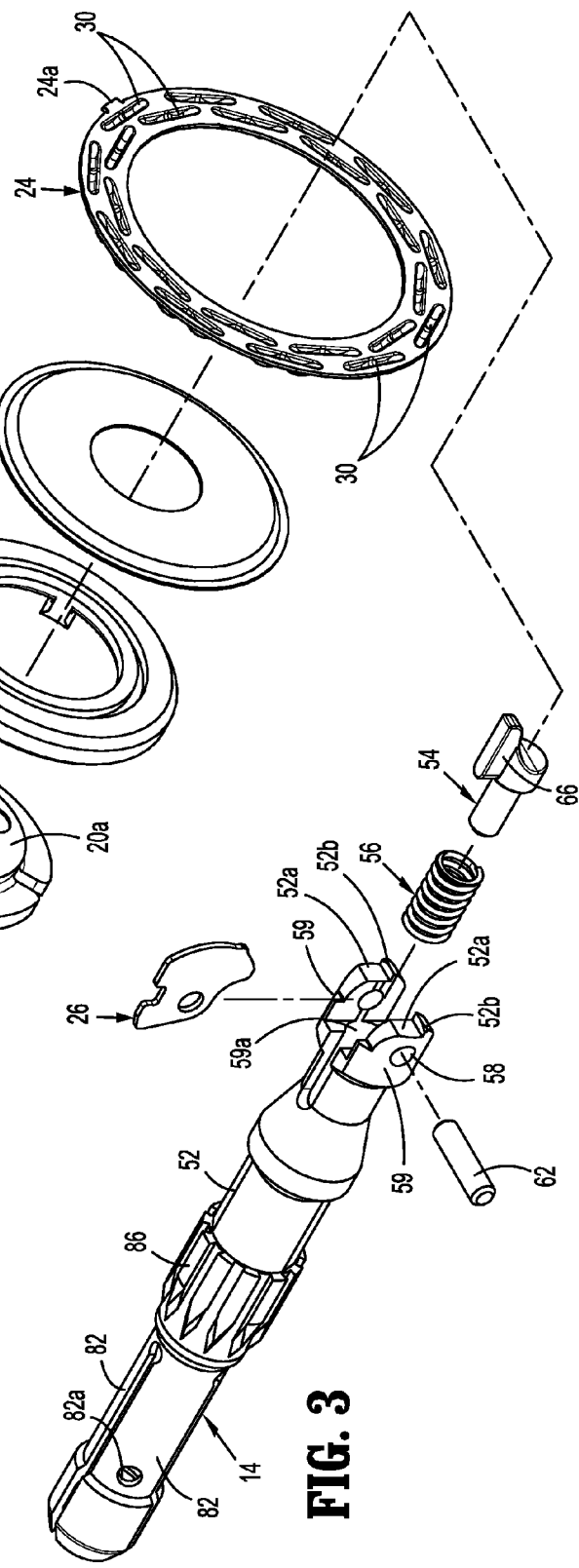

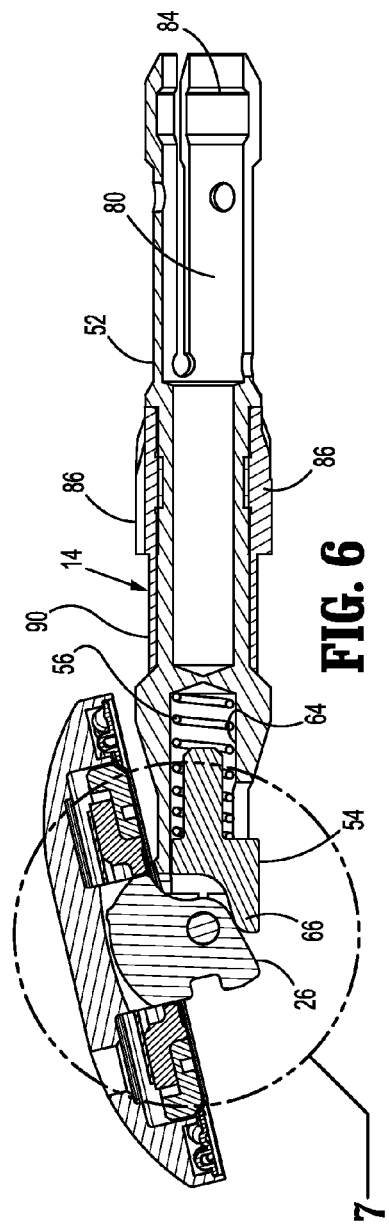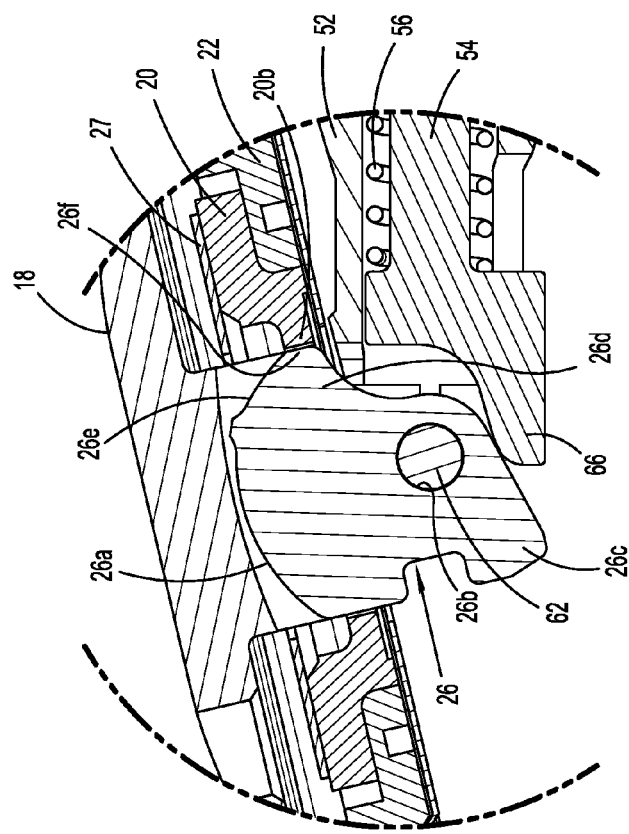

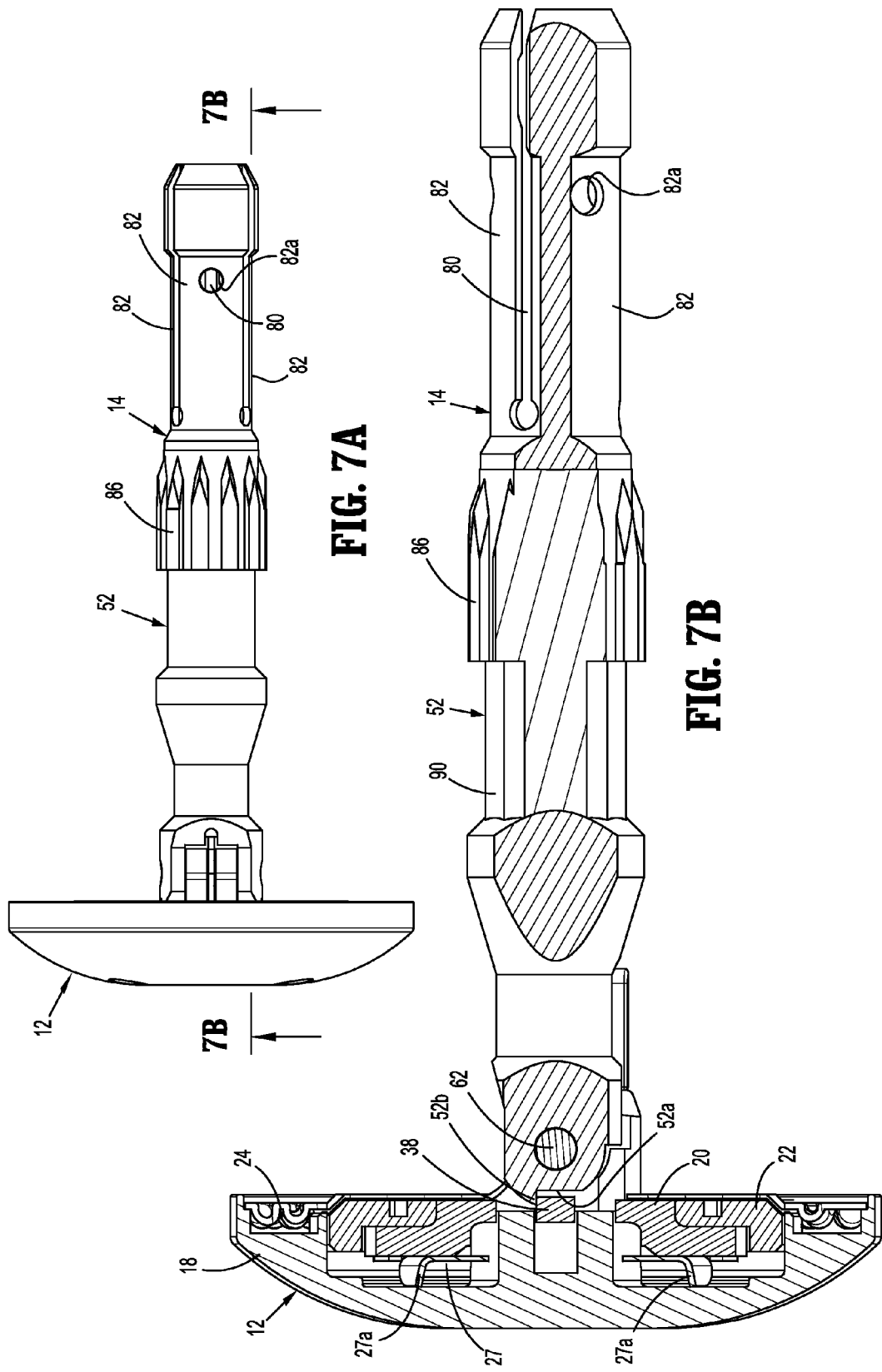

TILT ANVIL ASSEMBLY

BACKGROUND

1. Technical Field

The present disclosure relates generally to an anvil assembly which is suitable for use with a circular anastomosis stapler. More specifically, the present disclosure relates to an anvil assembly having a tiltable head which is suitable for use with a circular anastomosis stapler.

2. Background of Related Art

Circular anastomosis staplers which include an anvil assembly having a tiltable anvil head are known in the art. One such circular anastomosis stapler is disclosed in U.S. patent application Ser. No. 10/968,722 ("'722 application") which is incorporated herein by reference in its entirety. In some known circular anastomosis staplers, a backup plate located within the anvil assembly is positioned to prevent tilting of the anvil head of the anvil assembly prior to firing of the stapler. Upon firing of the stapler, a knife blade of the stapler engages and moves the backup plate to a position which allows the anvil head to tilt upon retraction of the knife blade. If the backup plate sticks to the knife blade upon retraction of the knife blade, the backup plate may return to its position preventing tilting of the anvil head. Thus, the anvil head will not tilt.

In order to prevent the backup member from sticking to the knife blade, the '722 application discloses a retainer clip which engages the backup plate upon retraction of the knife blade. Although, the retainer clip is effective, other devices for preventing retraction of the backup plate are desired.

SUMMARY

A tilt anvil assembly is disclosed which includes a center rod and an anvil head assembly including a housing, a post, an anvil plate having staple deforming pockets, and a backup member. The head assembly is pivotally secured to the center rod and pivotal in relation to the center rod between a non-tilted position and a tilted position. The backup member is movable about the post from a first position in which a portion of the backup member is positioned to prevent movement of the head assembly from the non-tilted position to the tilted position to a second position in which the backup member is positioned to accommodate movement of the head assembly in relation to the center rod from the non-tilted position to the tilted position. The anvil assembly further includes a pivotal latch member positioned in the head assembly to prevent movement of the backup member from the second position to the first position.

In one embodiment, the head assembly is pivotally secured to the center rod about a pivot member and the pivotal latch member is pivotally mounted about the pivot member. The pivotal latch member is spring loaded and positioned to engage an inner periphery of the backup member when the backup member is in the non-tilted position. When the backup member is moved to its second position, the latch member is urged by the spring to a position engaging and in front of the backup member to urge the head assembly to the tilted position and prevent movement of the backup member from the second position to the first position.

In one embodiment, the anvil assembly further includes a retainer member positioned in the head assembly to prevent movement of the backup member from the first position to the second position until a predetermined force has been applied to the backup member. The predetermined force is between about ten pounds and about ninety pounds. The retainer member can include a deformable member which is positioned in the head assembly between the housing and the backup member. In one embodiment, the housing and the post define an annular recess and the retainer member is positioned in the annular recess. The retainer member can include an annular body which is positioned about the post and a plurality of deformable tabs extending therefrom. The backup member is positioned to abut the retainer member such that upon movement of the backup member from its first position to its second position, the deformable tabs are deformed.

In one embodiment, the backup member includes a cutting ring and a backup plate. The cutting ring can be secured to a proximal face of the backup plate. The backup plate can include at least one finger positioned to engage a distal surface of the center rod when the backup member is in its first position to prevent pivotal movement of the head assembly in relation to the center rod. The cutting ring can be formed from a softer material than the backup plate. In one embodiment, the cutting ring is formed from polyethylene and the backup plate is formed from a metal.

BRIEF DESCRIPTION OF THE DRAWINGS

Various embodiments of the presently disclosed tilt anvil assembly are disclosed herein with reference to the drawings wherein:

FIG. 1 is a side perspective view from one end of the presently disclosed tilt anvil assembly with the anvil head tilted;

FIG. 2 is a side perspective view from the other end of the tilt anvil assembly shown in FIG. 1;

FIG. 3 is a side perspective view with parts separated of the tilt anvil assembly shown in FIG. 2;

FIG. 4 is a side perspective view of the cam latch member of the tilt anvil assembly shown in FIG. 3;

FIG. 5 is a side perspective view of the retainer member of the tilt anvil assembly shown in FIG. 3;

FIG. 6 is a side cross-sectional view of the tilt anvil assembly shown in FIG. 1 with the anvil head in the tilted position.

FIG. 7 is an enlarged view of the indicated area of detail shown in FIG. 6;

FIG. 7A is a side view of the tilt anvil assembly shown in FIG. 1 with the anvil head in the non-tilted position;

FIG. 7B is a cross-sectional view taken along section lines 7B-7B of FIG. 7A;

DETAILED DESCRIPTION OF EMBODIMENTS

Figure 9:
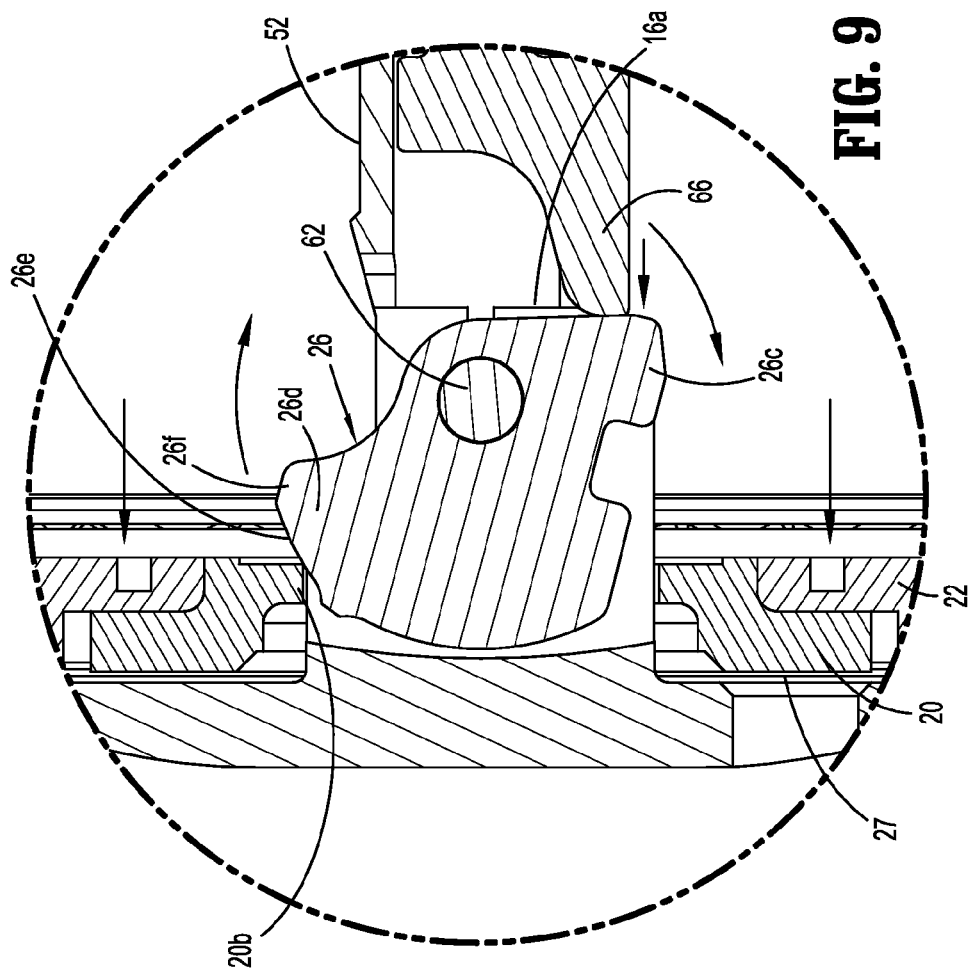
FIG. 9 is an enlarged view of the indicated area of detail shown in FIG. 8.

Embodiments of the presently disclosed tilt anvil assembly 10 will now be described in detail with reference to the drawings in which like reference numerals designate identical or corresponding elements in each of the several views.

FIGS. 1-10 illustrate a tilt anvil assembly 10 which is suitable for use with a surgical stapling device for performing, for example, circular anastomoses of hollow tissue organs and hemorrhoid surgeries. Referring to FIGS. 1-3, anvil assembly 10 includes a head assembly 12 and a center rod assembly 14. Head assembly 12 includes a post 16, a housing 18, a backup member or plate 20, a cutting ring 22, a cutting ring cover 23, an anvil plate 24, a cam latch member 26, and a retainer member 27. Post 16 is monolithically formed with and centrally positioned within head 18. Alternately, head 18 and post 16 may be formed separately and fastened together using a known fastening technique, e.g., welding. Anvil plate 24 is supported in an outer annular recess 28 (FIG. 3) of housing 18 and includes a plurality of staple deforming pockets 30 for receiving and deforming staples. At least one tab 24a extends radially outwardly from anvil plate 24 and is received within a cutout 32 formed in an outer rim of housing 18. Tab 24a and cutout 32 function to align or properly position anvil plate 24 within annular recess 28 of housing 18.

Referring to FIG. 3, backup plate 20 includes a central opening 34 which is positioned about post 16 within an inner annular recess 36 of housing 18 between post 16 and outer annular recess 28. Backup plate 20 includes a raised platform 20a. Cutting ring 22 includes an opening 22a having a configuration substantially the same as platform 20a. Although platform 20a is illustrated as having a circular shape, other configurations are envisioned, e.g., square, rectangular, triangular, etc. In one embodiment, cutting ring 22 is formed from polyethylene and is fixedly secured to backup plate 20 using, for example, an adhesive, to form a backup plate/cutting ring assembly. Backup plate 20 is formed from a hard material, e.g., a metal. Alternately other materials of construction may be used to construct backup plate 20 and cutting ring 22. Further, backup plate 20 and cutting ring 22, in the alternative, can be formed as a single or unitary structure.

A cutting ring cover 23 is secured to a outwardly facing or proximal surface 40 of cutting ring 22 using, for example, an adhesive. In one embodiment, cutting ring cover 23 is formed from a material or materials, which have a hardness greater than that of the cutting ring, e.g., mylar. In one embodiment, cutting ring cover 23 includes two layers of mylar (not shown) which are joined together using an adhesive and a polypropylene coating. Alternately, cutting ring 22 need not have a cover. Cutting ring 22 and backup plate 20 are slidably mounted about post 16. Backup plate 20 includes a pair of inwardly extending fingers 38 which will be described in further detail below.

Retainer member 27 is positioned in inner annular recess 36 between backup plate 20 and a back wall 18a (FIG. 3) of housing 18. In one embodiment, retainer member 27 is annular and includes a plurality of deformable tabs 27a which engage a rear surface of backup plate 20. Retainer member 27 prevents backup plate 20 and cutting ring 22 from moving or being pushed into inner annular recess 36 of housing 18 until a predetermined force sufficient to deform tabs 27a has been applied to the backup plate/cutting ring assembly. The predetermined force can be close to but is less than the force applied by an annular cutting blade of a surgical stapling device when it engages, for example, the cutting ring of anvil assembly 10. The predetermined force is preferably between about ten pounds and about ninety pounds and is most preferably about thirty (30) pounds. When the predetermined force is reached, e.g., during cutting of tissue, backup plate 20 is urged into inner annular recess 36 and compresses retainer member 27. It is envisioned that other crushable, deformable, collapsible or movement restricting members may be used to retain the backup plate/cutting ring assembly in a fixed position until a predetermined force has been applied to the backup plate/cutting ring assembly.

Anvil center rod assembly 14 includes a center rod 52, a plunger 54 and plunger spring 56. A first end of center rod 52 has a pair of arms 59 which define a cavity 59a (FIG. 3). Each arm 59 has a transverse throughbore 58 which is aligned with a central longitudinal axis of center rod 52. Alternately, throughbores 58 can be offset from the longitudinal axis of center rod 52. Post 16 of anvil head assembly 12 is dimensioned to be positioned within cavity 59a and also includes a transverse throughbore 60. A pivot member 62 pivotably secures post 16 to center rod 52 via throughbores 58 and 60 such that anvil head assembly 12 is pivotably mounted to anvil center rod assembly 14.

Referring to FIGS. 3 and 6-9, cam latch member 26 includes a body 26a having a throughbore 26b. Throughbore 26b is dimensioned to receive pivot member 62 such that cam latch member 26 is pivotally mounted within transverse slot 72 (FIG. 3) of post 16 about pivot member 62. As shown in FIGS. 4, 6 and 7 (see also FIG. 2), cam latch member 26 includes a first body portion 26c which extends partially from slot 72 of post 16 and is positioned to be engaged by finger 66 of plunger 54. Cam latch member 26 also includes an edge 26f which is urged into engagement with an inner periphery of backup plate 20 by finger 66 of plunger 54 when anvil head 12 is in its non-tilted or operative position.

Plunger 54 is slidably positioned in a bore 64 (FIG. 6) formed in the first end of center rod 52. Plunger 54 includes an engagement finger 66 which is offset from the pivot axis of anvil head assembly 12 and biased into engagement with an edge 26c of cam latch 26. As will be discussed in further detail below, engagement of finger 66 with edge 26c of cam latch 26 presses edge 26f against an inner periphery of back plate 20 to urge anvil head assembly 12 to a pivoted or tilted position on center rod 52. In a preferred position, fingers 38 formed on backup plate 20 engage protrusions 52b adjacent top surface 52a of center rod 52 to prevent anvil head assembly 12 from pivoting about pivot member 62. When anvil assembly 10 is attached to a surgical stapling device and the device is fired such as disclosed in the manner described in the '722 application, backup plate 20 and cutting ring 22 are pushed into inner annular recess 36 of housing 18 about post 16 by a knife blade (not shown) to move fingers 38 away from and out of engagement with protrusions 52b of center rod 52 (FIG. 10) and permit plunger 54 to pivot anvil head assembly 12 about pivot member 62. Retainer member 27 prevents inadvertent or premature movement of backup plate 20 into inner-annular recess 36 to prevent premature or inadvertent tilting of anvil head assembly 12.

Referring to FIGS. 7A and 7B, a second end of center rod 52 includes a bore 80 defined by a plurality of flexible arms 82. Flexible arms 82 each include an opening 82a dimensioned to receive a projection formed on or connected to a removable trocar (not shown) or the like. The distal ends of each of flexible arms 82 include an internal shoulder 84 (FIG. 6) dimensioned to releasably engage the anvil retainer of a surgical stapling device (not shown) to secure anvil assembly 10 to the surgical stapling device. A plurality of splines 86 are formed about center rod 52. Splines 86 function to align anvil assembly 10 with the staple holding portion of a surgical stapling device. Center rod 52 also includes an annular recessed portion 90 to facilitate grasping of anvil assembly 10 by a surgeon with a grasper. Recessed portion 90 may include a roughened or knurled surface or an overmold to facilitate grasping of anvil assembly 10.

Referring to FIGS. 6-7B, when anvil assembly 10 is in its preferred non-tilted position, backup plate 20 is spaced from back wall 18a of housing 18 by retainer 27 and protrusions 52b of center rod 52 engage fingers 38 of backup plate 20 to prevent tilting of anvil head assembly 12 about pivot member 62. As shown in FIG. 7, finger 66 of plunger 54 is urged by spring 56 into engagement with body portion 26c of cam latch member 26 to urge cam latch member 26 in a clockwise direction about pivot member 62 such that edge 26f of cam latch member 26 engages an inner periphery 20b of backup member 20.

Figure 8:
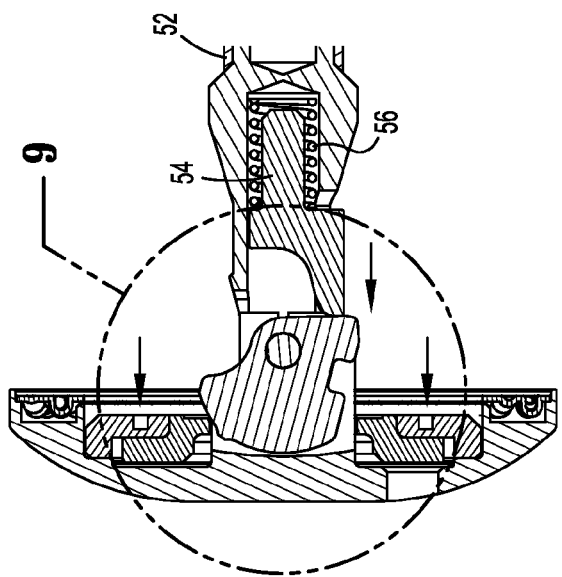
FIG. 8 is a side cross-sectional view of the anvil head and distal end of the anvil center rod taken through the cam latch member prior to tilting of the anvil head with the backup plate and cut ring in their advanced position in the anvil head housing.
Figure 9A:
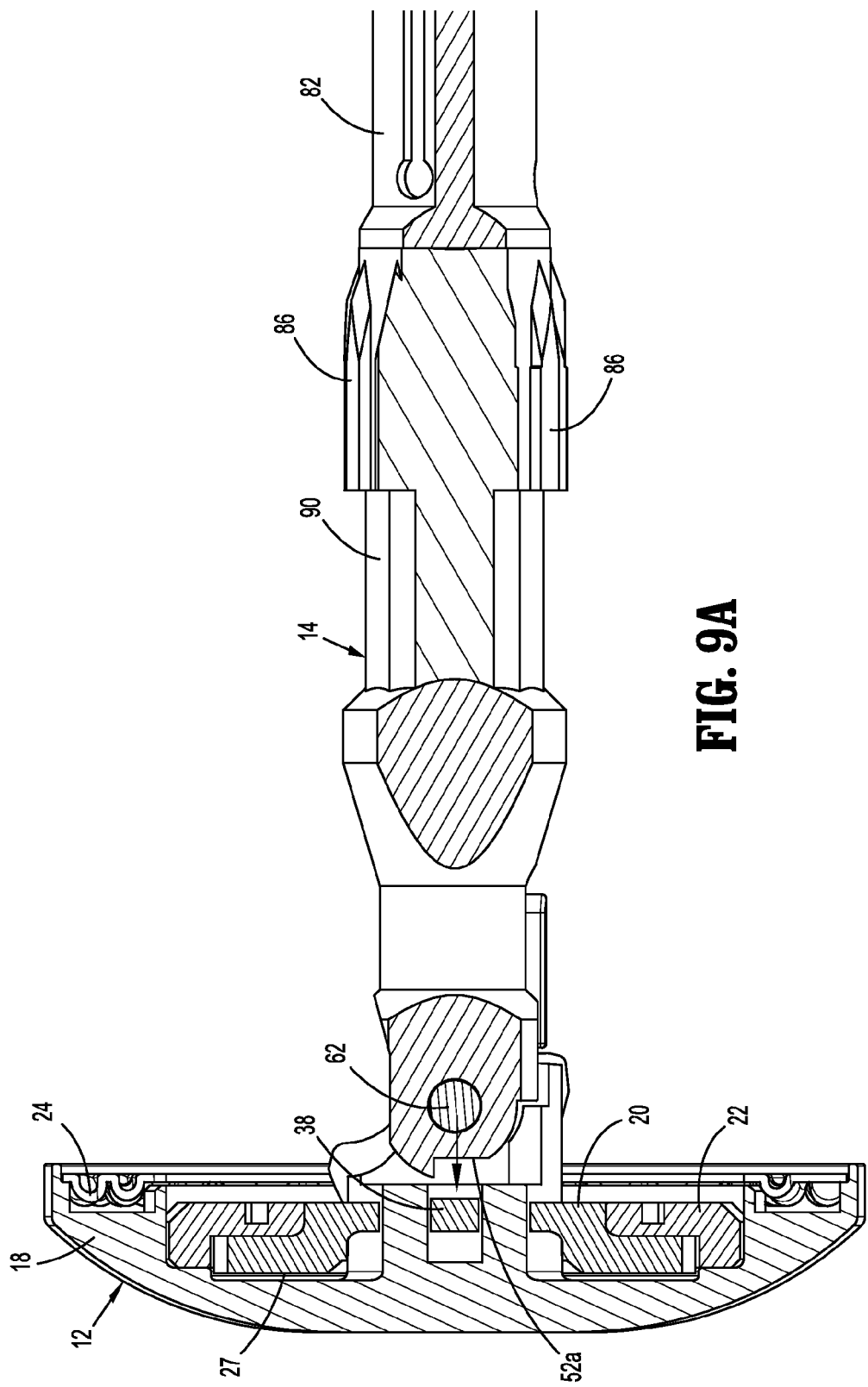
FIG. 9A is a side cross-sectional view of the anvil assembly shown in FIG. 8 taken through an arm of the anvil center rod.

Referring to FIGS. 8-9A, when anvil assembly 10 is attached to a stapling device and the device is fired, a knife blade (not shown) of the stapling device engages cutting ring 22 to move cutting ring 22 and backup plate 20 in the direction indicated by arrow "W" in FIG. 9 into annular recess 36 of housing 18 of anvil head assembly 12. When this occurs, deformable tabs 27a are deformed against back wall 18a of housing 18 and fingers 38 of backup member 20 move away from protrusions 52b of center rod 52. Further, inner periphery 20b of backup plate 20 moves past edge 26f of cam latch member 26 such that cam latch member 26 is pivoted in the direction indicated by arrow "X" in FIG. 9 by plunger 54 to a position in which body portion 26d is positioned in front of and engages backup plate 20. Engagement of plunger 54 with cam latch member 26 and subsequently with post 16 urges anvil head assembly 12 to the tilted position. It is noted that anvil head assembly 12 will not immediately tilt upon firing of a stapling device (not shown) because, upon firing, anvil head assembly 12 is in an approximated position, i.e., the anvil head assembly 12 is in close alignment with the shell assembly of the stapling device (not shown). As such, the anvil head assembly 12 will only begin to tilt when the anvil head assembly and the shell assembly of the stapling device (not shown) are being unapproximated.

Figure 10:
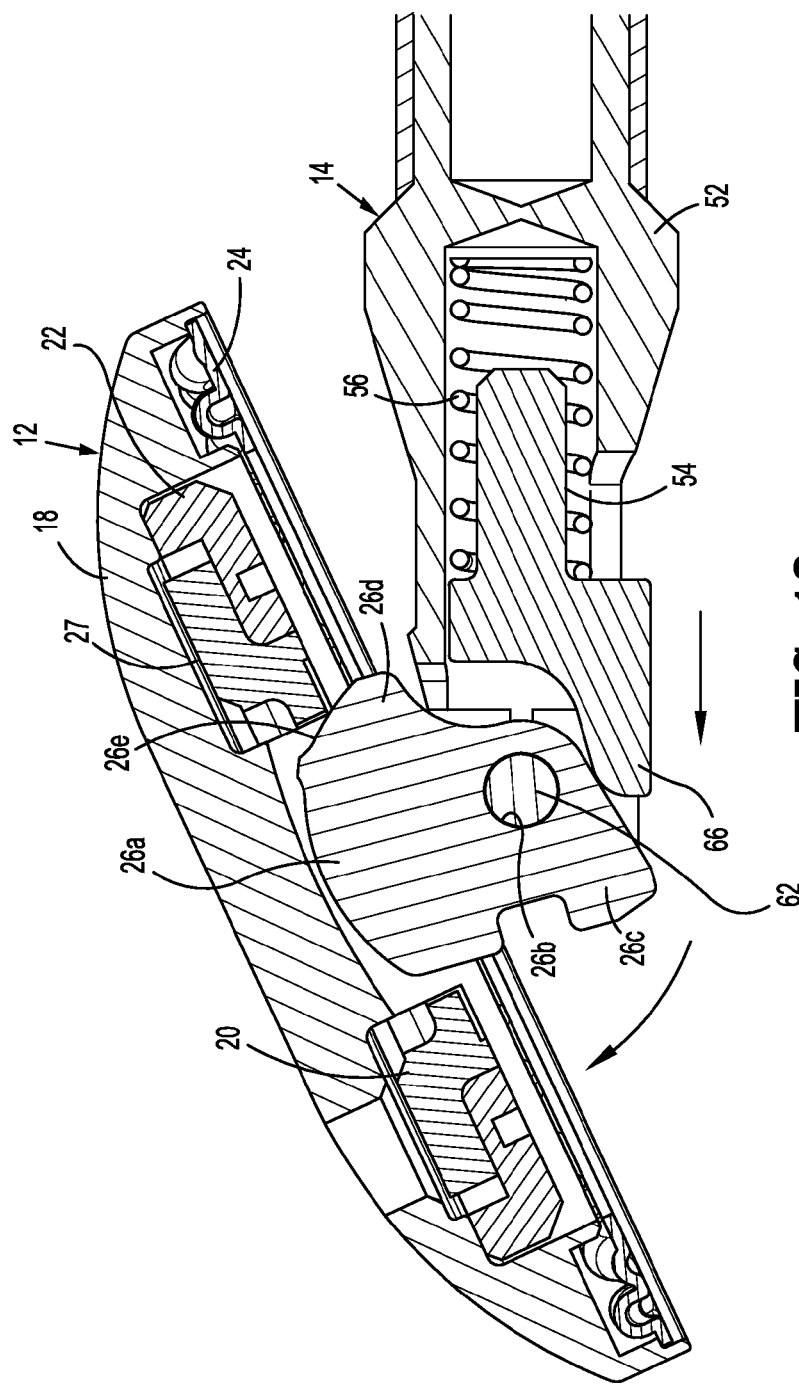
FIG. 10 is a side cross-sectional view of the anvil head and distal end of the anvil center rod taken through the cam latch member as the anvil head pivots from the non-tilted position to the tilted position.

Referring to FIG. 10, as anvil head assembly 12 pivots towards its tilted position, finger 66 of plunger 54 maintains surface 26e of cam latch member 26 in contact with backup plate 20 to prevent backup plate 20 from sticking to the knife blade as the knife blade is retracted. It is noted that curved surface 26e of cam latch member is configured to eliminate any gap and ensure contact between surface 26e of cam latch member 26 and backup plate 20 to hold backup plate 20 in place during and after the knife blade is retracted such that the cutting ring and backup plate assembly stay in their correct position during tilting of anvil assembly 12.

It will be understood that various modifications may be made to the embodiments disclosed herein. For example, the cutting ring and backup plate can be unitarily or integrally formed. Further, the anvil assembly need not have cutting ring cover. Therefore, the above description should not be construed as limiting, but merely as exemplifications of preferred embodiments. Those skilled in the art will envision other modifications within the scope and spirit of the claims appended hereto.

What is claimed is:

1. A tilt anvil assembly comprising:
   a center rod;
   a head assembly including a housing, a post, an anvil plate having staple deforming pockets, and a backup member, the head assembly being pivotally secured to the center rod and pivotal in relation to the center rod between a non-tilted position and a tilted position, wherein the backup member is movable about the post from a first position in which a portion of the backup member is positioned to prevent pivotal movement of the head assembly from the non-tilted position to the tilted position, to a second position in which the backup member is positioned to permit pivotal movement of the head assembly in relation to the center rod from the non-tilted position to the tilted position, and the head assembly further including a pivotal latch member which is urged by a biasing member into engagement with an inner peripheral surface of the backup member when the backup member is in the second position to prevent movement of the backup member from the second position to the first position.

2. A tilt anvil assembly according to claim 1, wherein the head assembly is pivotally secured to the center rod about a pivot member, the pivotal latch member being pivotally mounted about the pivot member.

3. A tilt anvil assembly according to claim 1, wherein the pivotal latch member is configured to maintain engagement with the backup member when the head assembly moves from the non-tilted position to the tilted position such that movement of the backup member from its second position towards its first position is prevented.

4. A tilt anvil assembly according to claim 1, wherein the pivotal latch member is positioned to engage an inner periphery of the backup member when the backup member is in its first position.

5. A tilt anvil assembly according to claim 4, further including a plunger which is urged by the biasing member into engagement with the pivotal latch member to urge the pivotal latch member into engagement with the backup member.

6. A tilt anvil assembly according to claim 5, wherein the pivotal latch member includes a curved surface which is configured to eliminate any gap between the pivotal latch member and the backup member during movement of the head assembly from the first position to the second position.

7. A tilt anvil assembly according to claim 1, further including a retainer member positioned in the head assembly to prevent movement of the backup member from the first position to the second position until a predetermined force has been applied to the backup member.

8. A tilt anvil assembly according to claim 7, wherein the retainer member includes a deformable member which is positioned in the head assembly between the housing and the backup member.

9. A tilt anvil assembly according to claim 8, wherein the housing and the post define an annular recess, the retainer member being positioned in the annular recess.

10. A tilt anvil assembly according to claim 9, wherein the retainer member includes an annular body which is positioned about the post and a plurality of deformable tabs extending therefrom.

11. A tilt anvil assembly according to claim 10, wherein the backup member is positioned to abut the retainer member such that upon movement of the backup member from its first position to its second position, the deformable tabs of the retainer member are deformed.

12. A tilt anvil assembly according to claim 1, wherein the backup member includes a cutting ring and a backup plate, the cutting ring being secured to a proximal face of the backup plate.

13. A tilt anvil assembly according to claim 12, wherein the backup plate includes at least one finger positioned to engage a surface of the center rod when the backup member is in its first position to prevent pivotal movement of the head assembly in relation to the center rod.

14. A tilt anvil assembly according to claim 13, wherein the cutting ring is formed from a softer material than the backup plate.

15. A tilt anvil assembly according to claim 14, wherein the cutting ring is formed from polyethylene and the backup plate is formed from a metal.

16. A tilt anvil assembly according to claim 7, wherein the predetermined force is between about ten pounds and about ninety pounds.

17. A tilt anvil assembly according to claim 1, wherein the center rod defines a longitudinal axis and a pivot axis of the head assembly intersects the longitudinal axis of the center rod.

* * * * *